United States Patent [19]

Freskos et al.

[11] Patent Number: 4,914,233
[45] Date of Patent: Apr. 3, 1990

[54] SYNTHESIS OF BETA-THYMIDINE

[75] Inventors: John N. Freskos; K. Pushpananda A. Senaratne, both of Baton Rouge, La.

[73] Assignee: Ethyl Corporation, Richmond, Va.

[21] Appl. No.: 162,508

[22] Filed: Mar. 1, 1988

[51] Int. Cl.$^4$ .............................................. C07H 1/00
[52] U.S. Cl. ...................................... 536/23; 536/4.1; 536/18.4
[58] Field of Search ........................................... 536/23

[56] References Cited

U.S. PATENT DOCUMENTS

| | | | |
|---|---|---|---|
| 3,709,874 | 1/1973 | Moffatt et al. | 536/23 |
| 3,748,320 | 7/1973 | Vorbruggen et al. | 536/23 |
| 3,873,516 | 3/1975 | Kotick et al. | 536/23 |
| 4,103,082 | 7/1978 | Suami | 536/16.6 |

OTHER PUBLICATIONS

Johnson and Hilbert, Science, 1929, Vol. LXIX, pp. 579–580.
Villars, The Journal of the American Chemical Society, 1930, vol. 52, pp. 2001–2007.
Burckhalter et al., J. Amer. Pharm. Assoc., 1955, vol. 44, pp. 545, 550.
Hoffer, Chem. Ber., 1960, vol. 93, pp. 2777–2781.
Barker, et al., J. Org. Chem., 1961, vol. 26, pp. 4605–4609.
Codington, et al., J. Org. Chem., 1964, vol. 29, pp. 558–564.
Nishimura et al., Chemical and Pharmaceutical Bulletin, 1964, vol. 12, pp. 352–356.
Wittenburg, Z., Chem., 1964, vol. 4, No. 8, pp. 303–304 (Translation Provided).
Hampton et al., Biochemistry, 1966, vol. 5, pp. 2076–2082.
Guthrie et al., Chemistry and Industry, 1968, pp. 547–548.
Pierce, "Silylation of Organic Compounds", 1968, Pierce Chemical Company, Rockford, Ill., pp. 18–26.
Wittenburg, Chem. Ber. 1968, vol. 101, pp. 1095–1114.
Kotick et al., J. Org. Chem., 1969, vol. 34, pp. 3806–3813.
Niedballa et al., J. Org. Chem., 1974, vol. 39, pp. 3654–3674.
Niedballa et al., J. Org. Chem. 1976, vol. 41, pp. 2084–2086.
Skulnick, J. Org. Chem., 1978, vol. 43, pp. 3181–3194.
Vorbruggen, et al., Chem. Ber., 1981, vol. 114, pp. 1256–1268.
"Chemistry and Biology of Nucelosides and Nucleotides", edited by R. E. Harmon, R. K. Robis and L. B. Townsend, Academic Press, Inc., New York, N.Y., copyright 1978.
Hubbard et al., Nucleic Acids Research, 1984, vol. 12, pp. 6827–6837.
Kuszmann, Carbohydrate Research, 1985, vol. 142, pp. 71–84.
Ozaki et al., Bull. Chem. Soc. Japan, vol. 50(8), 2197–2198 (1977).
Guthrie et al., Chemistry and Industry, pp. 547–548 (1968).

Primary Examiner—Johnnie R. Brown
Assistant Examiner—James O. Wilson
Attorney, Agent, or Firm—J. F. Sieberth

[57] ABSTRACT

A process is provided in which a mixture of alpha- and beta-anomers is converted selectively to the desired beta-thymidine. The process involves the following steps: (a) converting a mixture of alpha- and beta-anomers of tetra-O-acylribofuranose to tri-O-acyl-β-ribothymidine; (b) converting tri-O-acyl-β-ribothymidine to β-ribothymidine; (c) converting β-ribothymidine to 2,2'-anhydro-β-thymidine; (d) converting 2,2'-anhydro-β-thymidine to 2'-halo-2'-deoxy-5-methyluridine; and (e) converting 2'-halo-2'-deoxy-5-methyluridine to beta-thymidine. The mixture of alpha- and beta-anomers of tetra-O-acylribofuranose may be produced by any suitable procedure such as by converting lower alkyl ribofuranoside to the tetra-O-acylribofuranose mixture. The lower alkyl ribofuranosides may in turn be produced by various methods. However, a desirable way of effecting this conversion involves use of D-ribose as the starting material which is converted to the lower alkyl ribofuranoside.

20 Claims, No Drawings

SYNTHESIS OF BETA-THYMIDINE

TECHNICAL FIELD

This invention relates to a novel and useful process for the synthesis of beta-thymidine.

BACKGROUND

Beta-thymidine is of interest in the synthesis of pharmaceuticals useful, for example, in the treatment of patients suffering from acquired immunodeficiency syndrome (AIDS).

Known processes for synthesizing beta-thymidine, while operable, tend to be tedious, time-consuming, and expensive. For example, a common way of producing beta-thymidine involves a coupling reaction between protected deoxyribose and a protected thymine. Unfortunately, this route results in the formation of mixed alpha- and beta-anomers of the protected thymidine. Note in this connection A. J. Hubbard, et al. *Nucleic Acids Research*, 1984, 12, 6827 et seq.; U. Nieballa, et al. *J. Org Chem.* 1974. 39, 3654 et seq.; and H. Vorbruggen, et al. U.S. Pat. No. 3,748,320. Since the alpha-anomer is not useful for the intended purpose, it must be separated from the beta-anomer. In addition, the formation of the alpha-anomer results in loss of raw materials and reduced process efficiency. Inasmuch as deoxyribose is a relatively expensive starting material, its loss due to formation of the alpha-anomer results in economic penalties which are not inconsequential.

A process which would selectively produce the desired beta-anomer would be a welcome contribution to the art. This invention is believed to fulfill this need in an expeditious, efficient and economical manner.

THE INVENTION

In accordance with this invention, a process is provided in which a mixture of alpha- and beta-anomers is converted selectively to the desired beta-thymidine. This process involves the following steps:
(a) converting a mixture of alpha- and beta-tetra-O-acyl ribofuranose to tri-O-acyl ribothymidine;
(b) converting tri-O-acyl ribothymidine to ribothymidine;
(c) converting ribothymidine to 2,2'-anhydrothymidine;
(d) converting 2,2'-anhydrothymidine to 2'-halo-2'-deoxy-5-methyluridine; and
(e) converting 2'-halo-2'-deoxy-5-methyluridine to beta-thymidine.

The mixture of alpha- and beta-tetra-O-acyl ribofuranose may be produced by any suitable procedure such as by converting lower alkyl ribofuranoside to the tetra-O-acyl ribofuranose mixture. The lower alkyl ribofuranosides may in turn be produced by various methods. However, a desirable way of effecting this conversion involves use of D-ribose as the starting material which is converted to the lower alkyl ribofuranoside.

While other condensation reactions may be utilized, Step (a) above preferably involves a Lewis acid or Friedel-Crafts catalyzed condensation of the tetra-O-acyl ribofuranose mixture with a protected thymine. Accordingly, a preferred overall process sequence of this invention involves use as raw materials of D-ribose and thymine. Such overall synthesis may be depicted as follows:

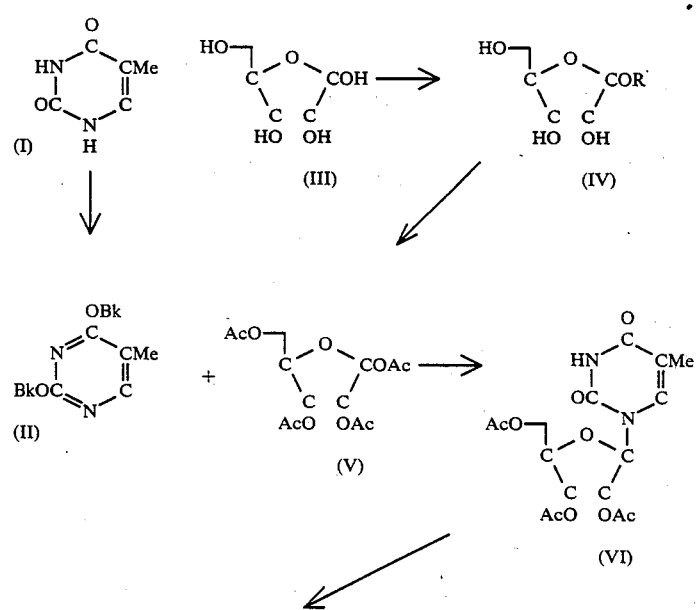

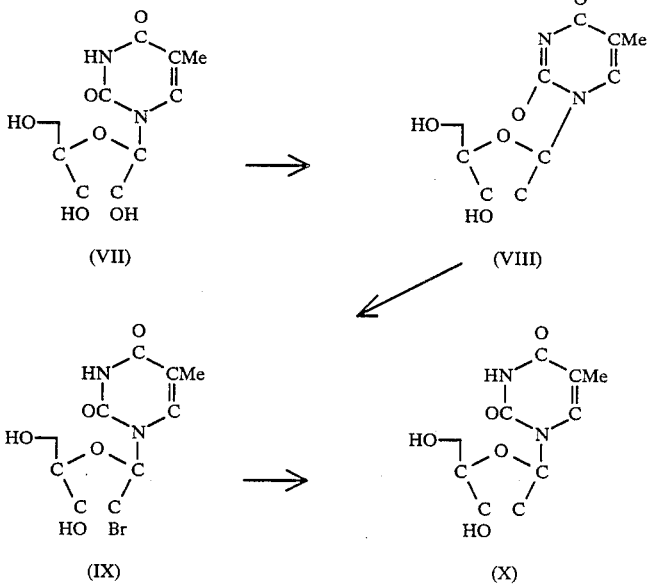

where Ac is an acyl group, Bk is a protecting group, Me is a methyl group, and R is a lower alkyl group.

The preferred synthetic reactions and conditions for each individual step of the above overall process are set forth below, the compounds being keyed to the formulas in the equations given hereinabove.

Converting Thymine (I) to a Protected Thymine (II)

While various protecting groups may be employed, it is preferred to employ silylated thymines. Thus in effecting this conversion thymine may be subjected to reaction conditions described in *Silylation of Organic Compounds,* Pierce Chemical Company, Rockford, Ill, 1968, pages 18–26, and in *Chem. Pharm. Bull.,* 12, 1964, 352 and *Z. Chem.,* 1964, 4, 303.

Suitable silylation reactions include trialkylchlorosilanes such as trimethylchlorosilane, triethylbromosilane, etc.; silazanes such as hexamethyldisilazane, etc.; N-silylated amines, such as trimethylsilylmethylamine, trimethylsilylaniline, trimethysilyldiethylamine, trimethysilylmethylimidazole, etc.; silylated amides; and the like.

Converting D-Ribose (III) to a Lower Alkyl Ribofuranoside (IV)

The preferred procedures for effecting this conversion are set forth in R. D. Guthrie, et al.. Chemistry and Industry. 1968. 547–548. In general, this procedure involves treating D-ribose in dry methanol or other anhydrous lower alcohol with sulfuric acid at low temperature followed by neutralization with dry pyridine. See also R. Barker. et al., *J. Org. Chem..* 1961, 26, 4605.

Lower alkyl ribofuranosides that may be produced in this manner include methylribofuranoside, ethylribofuranoside, propylribofuranoside, isopropylribofuranoside, butylribofuranoside, and the like.

Converting Lower Alkyl Ribofuranoside (IV) to an Anomeric Mixture of Tetra-0-Acyl Ribofuranose (V)

To produce a mixture of the alpha- and beta-anomers of tetra-O-acyl ribofuranose, the lower alkyl ribofuranoside is subjected to acylation using for example acetic anhydride, acetyl chloride, propionyl chloride, benzoyl chloride, or the like. The procedures for effecting such acylation reactions are standard and well known in the art. Note for example R. D. Guthrie, et al., supra.

It is interesting to note that in their above-referred to paper, R. D. Guthrie, et al. produce an anomeric mixture of tetra-O-acyl ribofuranose but then proceed to subject this mixture to a careful work-up procedure so as to isolate the beta-anomer therefrom. Such separation procedures are rendered totally unnecessary by the practice of this invention. Both anomers are converted to the desired ultimate product—beta-thymidine.

Converting an Anomeric Mixture of Tetra-O-Acyl Ribofuranose (V) to Tri-O-Acyl Ribothymidine (VI)

This conversion involves a Lewis acid (Friedel-Crafts) catalyzed condensation between the tetra-0-acyl ribofuranose anomeric mixture (V) and the protected thymine (II). The conditions for this condensation reaction are set forth in H. Vorbruggen et al., U.S. Pat. No. 3,748,320, and in U. Nieballa, et al. *J. Org. Chem.,* 1974, 39, 3654.

Converting Tri-O-Acyl Ribothymidine (VI) to Ribothymidine (VII)

For this conversion, based-catalyzed hydrolysis is used, normally at 0° to 100° C. While this hydrolysis can be effected by use of triethylamine in aqueous methanol, it has been found that catalytic amounts of sodium alkoxide in alcohol (e.g., sodium methoxide in methanol) at room temperature gives a cleaner product. Filtration through an ion exchange resin (e.g., Dowex 50 ion exchange resin) exchanges sodium cations for hydrogen, yielding pure ribothymidine.

Converting Ribothymidine (VII) to 2,2'-Anhydrothymidine (VIII)

In this process, a cyclization reaction occurs involving loss of water. A procedure for effecting this reaction is set forth in M. Kotick, et al., U.S. Pat. No. 3,873,516. Note especially Example 1 thereof.

In general, the process involves heating the ribothymidine with a dialkyl or diaryl carbonate in the presence of bicarbonate. The reaction may be conducted in various aprotic solvents having suitable boiling points, such as N,N-dimethylformamide (DMF), N,N-dimethylacetamide (DMAc), sulfolane, N-methylpyrrolidone, and the like.

Converting 2,2'-Anhydrothymidine (VIII) to 2'-Halo-2'-Deoxy-5-Methyluridine (IX)

To effect this conversion, the 2,2'-anhydrothymidine is subjected to halohydrogenation, most preferably hydrobromination, under standard conditions. See the patent to M. Kotick, et al. supra, especially Example 2 thereof. The reaction is preferably conducted in a solvent such as N,N-dimethylformamide (DMF), N,N-dimethylacetamide (DMAc), or the like. Temperatures in the vicinity of 100° C. are desirable, especially when using anhydrous HBr in the reaction.

Converting 2'-Halo-2'-Deoxy-5-Methyluridine (IX) to Beta-Thymidine (X)

The removal of halogen from the 2'-halo-2'-deoxy-5-methyluridine poses special problems due to the presence of two potentially reducible sites (the halogen atom and the double bond).

The standard method for effecting reductions in cases of this type involves refluxing the halogen-containing olefinically unsaturated reactant with a trialkyltin hydride such as tributyltin hydride, usually in an aromatic hydrocarbon solvent such as benzene, toluene or xylene containing a catalytic quantity of a radical initiator such as azobisisobutyronitrile (AIBN). See A. Holy, et al., *Coll. Czech. Chem. Commun.*, 1974, Volume 39, page 3157. While this method can be used in the overall process of this invention, its use is not recommended. Besides involving use of an expensive reductant, the removal of the by-product tin salts is a troublesome, tedious and time-consuming operation. Moreover, since tin salts tend to be toxic this method poses potential waste disposal problems.

It is definitely preferable to employ a selective reduction process in which the 2'-halo-2'-deoxy-5-methyluridine is hydrogenated at modest elevated pressure (e.g., 5 to 100 psi) in the presence of an aqueous slurry of Raney-nickel. It has been discovered by one of us (K.P.A.S.) that the double bond is unaffected in this reaction, the yields are high, and highly pure product can be produced.

The following examples are illustrative of the procedures used in the practice of this invention.

EXAMPLE 1

Converting Thymine (I) to a Protected Thymine (II)

A 250 mL round bottom flask equipped with magnetic stir bar, reflux condensor and nitrogen inlet was charged with 24 g (0.19M) of thymine, 120 mL of hexamethyldisilazane in 10 mL of N,N-dimethylformamide (DMF). The slurry was heated to 150° C. for 12 hours. The clear solution was cooled and excess of hexamethyldisilazane and DMF were distilled off at 60° C./45 mm. The product was then distilled to yield 47.1 g (92%) of white solid, O,O-bis(trimethylsilyl)thymine, bp 127°–131° C./16 mm.

EXAMPLE 2

Converting D-Ribose (III) to a Lower Alkyl Ribofuranoside (IV)

One mL of sulfuric acid was added to a solution of 5 g D-ribose in 80 mL of methanol. The solution was left in the refrigerator 15 hours then quenched by stirring with Amberlyst 21 resin. After filtration, the solution was concentrated in vacuo to yield 5.1 g (97%) of a thick golden syrup (methyl ribofuranoside).

EXAMPLE 3

Converting Lower Alkyl Ribofuranoside (IV) to an Anomeric Mixture of Tetra-O-Acyl Ribofuranose (V)

The crude syrup from Example 2 was dissolved in 20 mL of acetic anhydride, and 15 mL of acetic acid. The solution was cooled to 0° C. and 0.6 mL sulfuric acid was added. The reaction was stirred at room temperature for 1 hour, cooled to 0° C. and an additional 1 mL of sulfuric acid was added. After 2 hours at room temperature, the reaction was quenched by addition of 4 g sodium acetate and 50 mL ethanol. The mixture was concentrated to a stiff syrup and partitioned between 200 mL $CH_2Cl_2$ and 250 mL $H_2O$. The organic phase was washed with 90 mL brine, dried over $Na_2SO_4$ and concentrated in vacuo to a light amber semi-solid (8.75 g, 83%—from ribose). This product—a mixture of the alpha- and beta-anaomers of tetra-O-acetyl ribofuranose—was used without further purification.

EXAMPLE 4

Converting an Anomeric Mixture of Tetra-O-Acyl Ribofuranose (V) to Tri-O-Acyl Ribothymidine (VI)

A 500 mL round bottom flask equipped with magnetic stir bar and nitrogen inlet was charged with 46 g of tetra-O-acetyl ribofuranose, 48 g (1.2 eq) of O,O-bis(-trimethylsilyl)thymine and 170 mL of dichloroethane. To the slurry was added 17 mL (1 eq) of tin tetrachloride in 30 mL of dichloroethane. The homogenous yellow solution was stirred overnight at room temperature. After 16 hours, thin layer chromatography (TLC) (2% $MeOH/CH_2Cl_2$) showed no starting sugar. The reaction was quenched with 800 mL of saturated aqueous bicarbonate solution. The mixture was filtered through Celite to remove tin salts and, after separation, the organic phase was dried and concentrated to a light yellow foam (tri-O-acetyl ribothymidine) that was used directly in Example 5.

EXAMPLE 5

Converting Tri-O-Acyl Ribothymidine (VI) to Ribothymidine (VII)

Crude tri-O-acetyl ribothymidine from Example 4 was dissolved in 400 mL of methanol and 700 mg (0.25 eq) of sodium was added. After 12 hours, TLC (10% $MeOH/CH_2Cl_2$) showed only product formation. The reaction was quenched by filtration through a bed of Dowex 50. Concentration of the filtrate afforded 28.5 g (79% from tetra-O-acetyl ribofuranose) of a white solid (ribothymidine), mp 178°–180° C. Lit mp 183°–185° C.

EXAMPLE 6

Converting Ribothymidine (VII) to 2,2'-Anhydrothymidine (VIII)

A 100 mL round bottom flask equipped with magnetic stir bar, reflux condensor, and nitrogen inlet was charged with 5 g of ribothymidine, 4.7 g (1.2 eq) of diphenyl carbonate and 150 mg of sodium bicarbonate in 10 mL of DMF. The mixture was heated to 150° C. for 35 minutes. The black solution was diluted with 10 mL of MeOH and slowly added to 200 mL of diethyl ether. The tan product was filtered and dried to yield 4.4 g (96%) of anhydrothymidine.

EXAMPLE 7

Converting Ribothymidine (VII) to 2,2'-Anhydrothymidine (VIII)

Ribothymidine (2 g, 7.75 mmoles), NaHCO$_3$ (0.08 g, a catalytic amount) and diphenylcarbonate (2.1 g, 9.8 mmoles, Aldrich Co.) were mixed together in 10 mL of DMF and heated at 150° C. for 30 minutes under nitrogen. The dark amber colored solution was cooled and poured as a thin stream into vigorously stirred diethylether (200 mL). The product precipitated as a brownish powder. The stirring was continued for an additional 3 hours and the reaction mixture was filtered. The residue was washed with ether (2×75 mL) and air dried. The yield was 95% with an HPLC purity of 90–92%. Quantitative TLC purity was 87–88%.

EXAMPLE 8

Converting Ribothymidine (VII) to 2,2'-Anhydrothymidine (VIII)

Ribothymidine (2.1 g, 8.13 mmoles), NaHCO$_3$ (0.2 g) and diethylcarbonate (5.7 g, 48 mmoles) were dissolved in 20 mL of dimethylformamide and heated to 150° C. in a stainless steel autoclave for 5 to 6 hours. The internal pressure of the autoclave was 50–60 psi. The reaction mixtures was then distilled to remove excess diethylcarbonate and the resulting amber colored solution was poured slowly into vigorously stirred ether (400 mL). The stirring was continued for 5–6 hours and the precipitated anhydrothymidine was filtered. The isolated yield was 90–92%. The spectral (NMR) data were similar to samples made via the diphenylcarbonate route.

EXAMPLE 9

Converting 2,2'-Anhydrothymidine (VIII) to 2'-Halo-2'-Deoxy-5-Methyluridine (IX)

Anhydrothymidine (7.5 g, 0.031 moles) was dissolved in 32 mL of DMF containing 3.01 g of anhydrous HBr (0.037 moles) and kept at 100° C. for 40 minutes. The reaction system was cooled to room temperature, diluted with 24 mL of ethanol and slurried with 16 mL of Amberlyst 21 resin (slurried in water, Mallinckrodt, A21). The mixture was filtered to remove the resin and the resin was washed with 25 mL of water.

EXAMPLE 10

Converting 2'-Halo-2'-Deoxy-5-Methyluridine (IX) to Beta-Thymidine (X)

The aqueous washings and the filtrate from Example 9 (which contained the 2'-bromo-2'-deoxy-5-methyluridine) were combined and hydrogenated in a Parr apparatus at 20 psi in the presence of 8.0 g of Raney-nickel catalyst (a 50% slurry in water as received from Aldrich Co.). After 2–3 hours, the reaction mixture was filtered through a Celite filter pad. (The filtrate was slightly greenish in color indicating the presence of nickel salts). The Celite filter pad was washed with 30 mL of EtOH/H$_2$O. The washings and filtrate were combined and passed through Amberlite IR 120 resin (acidic form, Aldrich Co.) followed by Amberlyst 21 resin. The filtrate was then concentrated at reduced pressure to remove most of the aqueous alcohol and 50 mL of octane was added. The volume was reduced to half by azeotropically co-distilling the octane and DMF, (under reduced pressure, house vacuum). A gummy solid was left in the flask after decanting the remaining octane. This solid was refluxed with 75 ml of ethyl acetate to precipitate the beta-thymidine as a white powder. The solid was filtered and washed with 2×20 mL of ethyl acetate to give 6.1 g of product (81% yield). The mp was 182°–183.5° C. The product exhibited a specific rotation +30.3° at 25° C. in 1 N NaOH solution. Ignition at 800° C. for 1 hour gave 0.1% residue. An assay of product purity by a UV method indicated a purity of 101.0%.

This invention is susceptible to considerable variation in its practice within the spirit and scope of the appended claims.

We claim:

1. A process for producing beta-thymidine which comprises the steps of:
   (a) converting a mixture of alpha- and beta-anomers of tetra-O-acylribofuranose to tri-O-acyl-β-ribothymidine by reacting said mixture with a protected thymine;
   (b) hydrolyzing tri-O-acyl-β-ribothymidine to β-ribothymidine;
   (c) converting β-ribothymidine to 2,2,-anhydro-β-thymidine by reacting said β-ribothymidine with dialkyl or diaryl carbonate;
   (d) subjecting 2,2,-anhydro-β-thymidine to hydrohalogenation to produce 2,-halo-2'-deoxy-5-methyluridine; and
   (e) hydrogenating 2'-halo-2,-deoxy-5-methyluridine to produce beta-thymidine.

2. A process of claim 1 wherein said hydrohalogenation is hydrobromination and said 2'-halo-2'-deoxy-5methyluridine is 2'-bromo-2'-deoxy-5-methyluridine.

3. A process of claim 1 wherein the 2'-halo-2'-deoxy-5-methyluridine is converted to beta-thymidine by hydrogenation at a pressure in the range of about 5 to about 100 psi in the presence of a Raney-nickel catalyst.

4. A process of claim 3 wherein the Raney-nickel catalyst is employed as an aqueous slurry.

5. A process of claim 1 wherein said hydrohalogenation is hydrobromination and said 2'-halo-2'-deoxy-5methyluridine is 2'-bromo-2'-deoxy-5-methyluridine and wherein the 2'-bromo-2'-deoxy-5-methyluridine is converted to beta-thymidine by hydrogenation at a pressure in the range of about 5 to about 100 psi in the presence of a Raney-nickel catalyst.

6. A process of claim 5 wherein the Raney-nickel catalyst is employed as an aqueous slurry.

7. A process for producing beta-thymidine which comprises the steps of:
   (a) reacting D-ribose with a lower alkyl alcohol to produce a lower alkyl ribofuranoside;
   (b) subjecting a lower alkyl ribofuranoside to acylation to produce a mixture of alpha- and beta-anomers of tetra-O-acylribofuranose;
   (c) converting a mixture of alpha- and beta-anomers of tetra-O-acylribofuranose to tri-O-acyl-β-ribothymidine by reacting said mixture with a protected thymine;
   (d) subjecting tri-O-acyl-β-ribothymidine to base-catalyzed hydrolysis to produce β-ribothymidine;
   (e) converting β-ribothymidine to 2,2'-anhydro-β-thymidine by reacting said β-ribothymidine with dialkyl or diaryl carbonate;
   (f) subjecting 2,2,-anhydro-β-thymidine to hydrohalogenation to produce 2'-halo-2'-deoxy-5-methyluridine; and (g) reducing 2'-halo-2'-deoxy-5-methyluridine to produce beta-thymidine.

8. A process of claim 7 wherein said hydrohalogenation is hydrobromination and said 2'-halo-2'-deoxy-5-methyluridine is 2'-bromo-2'-deoxy-5-methyluridine.

9. A process of claim 7 wherein the 2'-halo-2'-deoxy-5-methyluridine is reduced to beta-thymidine by hydrogenation at a pressure in the range of about 5 to about 100 psi in the presence of a Raney-nickel catalyst.

10. A process of claim 9 wherein the Raney-nickel catalyst is employed as an aqueous slurry.

11. A process of claim 7 wherein said hydrohalogenation is hydrobromination and said 2'-halo-2'-deoxy-5-methyluridine is 2'-bromo-2'-deoxy-5-methyluridine and wherein the 2'-bromo-2'-deoxy-5-methyluridine is converted to beta-thymidine by hydrogenation at a pressure in the range of about 5 to about 100 psi in the presence of a Raney-nickel catalyst.

12. A process of claim 11 wherein the Raney-nickel catalyst is employed as an aqueous slurry.

13. A process for producing beta-thymidine which comprises the steps of:
    (a) reacting D-ribose with a lower alkyl alcohol to produce a lower alkyl ribofuranoside;
    (b) subjecting a lower alkyl ribofuranoside to acylation to produce a mixture of alpha- and beta-anomers of tetra-O-acylribofuranose;
    (c) reacting a mixture of alpha- and beta-anomers of tetra-O-acylribofuranose with a protected thymine to produce tri-O-acyl-β-ribothymidine;
    (d) subjecting tri-O-acyl-β-ribothymidine to hydrolysis to produce β-ribothymidine;
    (e) reacting β-ribothymidine with a dialkyl or diaryl carbonate to produce 2,2'-anhydro-β-thymidine;
    (f) subjecting 2,2'-anhydro-β-thymidine to hydrohalogenation to produce 2'-halo-2'-deoxy-5-methyluridine; and
    (g) Reducing 2'-halo-2'-deoxy-5-methyluridine by hydrogenation to produce beta-thymidine.

14. A process of claim 13 wherein said acylation is acetylation and said tetra-O-acylribofuranose is tetra-O-acetylribofuranose.

15. A process of claim 13 wherein β-ribothymidine is heated with a dialkyl or diaryl carbonate in the presence of bicarbonate to produce 2,2'-anhydro-β-thymidine.

16. A process of claim 13 wherein said hydrohalogenation is hydrobromination, and said 2'-halo-2'-deoxy-5-methyluridine is 2'-bromo-2'-deoxy-5-methyluridine.

17. A process of claim 13 wherein the 2'-halo-2'-deoxy-5-methyluridine is converted to beta-thymidine by hydrogenation at a pressure in the range of about 5 to about 100 psi in the presence of a Raney-nickel catalyst.

18. A process of claim 17 wherein the Raney-nickel catalyst is employed as an aqueous slurry.

19. A process of claim 13 wherein said hydrohalogenation is hydrobromination and said 2'-halo-2'-deoxy-5-methyluridine is 2'-bromo-2'-deoxy-5-methyluridine and wherein the 2'-bromo-2'-deoxy-5-methyluridine is converted to beta-thymidine by hydrogenation at a pressure in the range of about 5 to about 100 psi in the presence of a Raney-nickel catalyst.

20. A process of claim 19 wherein the Raney-nickel catalyst is employed as an aqueous slurry.

* * * * *

UNITED STATES PATENT AND TRADEMARK OFFICE
CERTIFICATE OF CORRECTION

PATENT NO. : 4,914,233

DATED : April 3, 1990

INVENTOR(S) : John N. Freskos et al.

It is certified that error appears in the above-identified patent and that said Letters Patent is hereby corrected as shown below:

Column 8, line 23 reads "to 2,2,-anhydro-" and should read
-- to 2,2'-anhydro --.

Column 8, line 26 reads "subjecting 2,2,-" and should read
-- subjecting 2,2'- --.

Column 8, line 27 reads "to produce 2,-halo-" and should read
-- to produce 2'-halo- --.

Column 8, line 29 reads "2'-halo-2,-deoxy" and should read
-- 2'-halo-2'-deoxy --.

Column 8, line 66 reads "2,2,-anhydro-" and should read
-- 2,2'-anhydro- --.

Signed and Sealed this

Fourth Day of February, 1992

Attest:

HARRY F. MANBECK, JR.

Attesting Officer

Commissioner of Patents and Trademarks